(12) United States Patent
Curtis

(10) Patent No.: US 6,709,862 B2
(45) Date of Patent: Mar. 23, 2004

(54) GROWING CELLS IN A RESERVOIR FORMED OF A FLEXIBLE STERILE PLASTIC LINER

(75) Inventor: Wayne R. Curtis, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/879,719

(22) Filed: Jun. 12, 2001

(65) Prior Publication Data

US 2001/0031491 A1 Oct. 18, 2001

Related U.S. Application Data

(62) Division of application No. 09/388,239, filed on Sep. 1, 1999, now Pat. No. 6,245,555.
(60) Provisional application No. 60/098,701, filed on Sep. 1, 1998, and provisional application No. 60/125,656, filed on Mar. 22, 1999.

(51) Int. Cl.[7] ............................. C12M 1/24; C12N 1/00
(52) U.S. Cl. .................... 435/325; 435/243; 435/289.1; 435/294.1; 435/292.1; 435/295.2; 435/304.1; 435/304.2; 435/410; 220/495.01; 220/495.05; 220/495.06; 220/495.11
(58) Field of Search ....................... 220/495.01, 495.05, 220/495.06, 495.11; 435/243, 289.1, 294.1, 292.1, 295.2, 304.1, 304.2, 325, 410, 383, 281.1, 800

(56) References Cited

U.S. PATENT DOCUMENTS

| | | |
|---|---|---|
| 1,709,701 A | 6/1929 | Althoff |
| 3,724,461 A | 4/1973 | Eisenberg |
| 3,934,999 A | 1/1976 | Meier |
| 3,946,780 A | 3/1976 | Sellers |
| 4,100,023 A | 7/1978 | McDonald |
| 4,647,539 A * | 3/1987 | Bach ........................... 435/284 |
| 4,797,367 A | 1/1989 | Pinder |
| 4,968,624 A | 11/1990 | Bacehowski et al. |
| 5,350,080 A | 9/1994 | Brown et al. |
| 5,534,417 A | 7/1996 | Arad et al. |
| 5,565,015 A | 10/1996 | Kobayashi |
| 5,591,350 A * | 1/1997 | Piechocki et al. .......... 210/764 |
| 5,614,412 A * | 3/1997 | Smith et al. .............. 435/305.1 |
| 6,245,555 B1 * | 6/2001 | Curtis |
| 6,297,046 B1 * | 10/2001 | Smith et al. |
| 2001/0049141 A1 * | 12/2001 | Fike et al. .................. 435/384 |

FOREIGN PATENT DOCUMENTS

| | | |
|---|---|---|
| EP | 0 343 885 | 6/1989 |
| GB | 1 380 316 | 1/1975 |
| GB | 2 202 549 | 6/1988 |
| JP | 63-36783 | 7/1986 |
| WO | 88/00965 | 6/1988 |
| WO | 90/02167 | 6/1990 |

* cited by examiner

*Primary Examiner*—David M. Naff
*Assistant Examiner*—Deborah K. Ware
(74) *Attorney, Agent, or Firm*—Stephen H. Eland; Dann, Dorfman, Herrell, Skillman, P.C.

(57) ABSTRACT

A method and apparatus for aseptic biological production of cells and/or microorganisms are provided. The apparatus includes a support housing having an interior chamber, a disposable flexible sterile plastic liner lining the interior chamber and a head plate attached to the liner forming a sealed chamber with the liner to form a reservoir. After use the liner can be thrown away and the apparatus can be reused with a new liner. In this way, the apparatus simplifies cleaning and ensuring validation required by pharmaceutical and food industry standards. Aerating fluid is introduced during culturing of cell or microorganisms in the reservoir. A growth characteristic can be used to vary flow rate and/or composition of the aerating fluid. Another reservoir may be used for circulation between two reservoirs.

27 Claims, 3 Drawing Sheets

GROWING CELLS IN A RESERVOIR FORMED OF A FLEXIBLE STERILE PLASTIC LINER

PRIORITY APPLICATIONS

This application is a divisional of application Ser. No. 09/388,239 filed on Sep. 1, 1999, now U.S. Pat. No. 6,245,555 B1. The present application also claims priority to U.S. Provisional Application No. 60/098,701 filed Sep. 1, 1998, No. 60/125,656 filed Mar. 22, 1999. Each of the foregoing applications are hereby incorporated herewith as if fully set forth herein.

FIELD OF THE INVENTION

The present invention relates to the field of biologic cell production. More specifically, the present invention relates to the aseptic production and processing of cells and/or microorganisms in a bioreactor.

BACKGROUND

The production of chemicals in bioreactor systems is expensive. The differential between production costs and product market value is the dominant driving force for drug discovery and development of potential bioprocesses. The importance of production costs is reflected in the economic observation that the volumetric productivity of a wide range of biologically produced products is about the same at $0.17 per liter per day. The expense of biological production is a motivation for pursuing chemical synthesis when possible; however, the complexity of synthesis of many natural products often makes this route equally costly. In the absence of chemical synthesis, metabolites derived from microorganisms must be produced in aseptic bioreactors. In contrast, plant-derived chemicals can be harvested from intact plants. Therefore, agronomic production or collection from natural environments is a formidable competitor to growth of plant tissues in bioreactor systems. Many rationales are given for pursuing plant tissue culture as a potential production system. The most compelling are those situations where intact plants are poor competitors. Some plants either grow very slowly, or are not amenable to agronomic production. In addition, environmental degradation is limiting the attractiveness of natural harvest, particularly from endangered environments such as the rain forest where the biochemical diversity is the greatest.

Although the bioreactor described herein is not limited to use for plant tissue culture, the economic constraints and stringent asepsis requirements presented by this production system provide an excellent context to demonstrate the effectiveness of the bioreactor. There have been many efforts to commercialize plant metabolites from cell culture; however, few have achieved commercial success. Low productivity is usually cited as the reason for failure despite the fact that production rates and tissue concentrations are very often substantially higher than the intact plant. In fact, tremendous productivities have been achieved by plant tissue culture. There are at least eight different systems where the metabolite levels are greater than 10% of the cell dry weight, and several of these productivities have been achieved with cultures that display relatively high growth rates. One example is anthocyanin pigments production by P.C.C. Technology, Japan where the cell content was greater than 17% and effective specific growth rates were 0.22 day$^{-1}$ at a scale of 500 L. Rosmarinic acid production was successfully scaled up by A Nattermann & Cie GmbH in a 30 L stirred tank. The titer of rosmarinic acid reached 5.5 g/L with volumetric productivity of nearly 1 g/L/day, and tissue content as high as 21% of dry weight. The failure of these processes is more a failure to compete economically with whole plant material rather than a failure of the cultures to be biochemically productive. There have also been significant advances in strategies to improve cellular productivity by cell line selection, genetic engineering, elicitation and root culture or enhance reactor productivity by operational strategies such as high density culture, integrated product recovery and immobilization. However, there is a limit to the improvements that can be achieved by these strategies, and for compounds where there is a low-cost alternative from intact plant material, it simply does not make sense to attempt production in bioreactor systems.

Despite the limitations, the potential of plant-tissue culture derived chemicals has resulted in a tremendous investment from both industry and academia in developing this technology. It has been demonstrated that large-scale production is technically feasible. The first commercial process was the production of shikonin. Since the market for this dye is limited, production has been on hold to focus efforts on taxol as a more profitable target. Similarly, the efforts of EscaGenetics on the production of vanillin were way-layed in favor of taxol development. Ginseng has been produced commercially by Nitto Denko (Japan) for 10 years at a scale of 25,000 liters. There are other reports of industrial scale cultivation of plant cells including tobacco at 15,500 L and three different plant species by DIVERSA (Hamburg, Germany) up to 75,000 L. Taxus sp. is being grown at industrial scale by both Phyton, Inc. and Sam Yang. These examples show that technical problems of scale-up can be overcome.

The preceding indicates that the technology for production of chemicals by plant tissue culture is available provided the secondary metabolite has a sufficiently high value. The required product price to consider plant tissue culture production has been estimated to be in the range of $1000 to $5000 per Kg. The issue arises as to whether this technology can be extended to lower value/higher volume biochemical production. To achieve this objective, it is useful to understand what contributes to production costs.

Based on experience with the commercial development of shikonin, the Mitsui group estimated that 64% of the production costs for cultured plant cells was due to fixed costs (depreciation, interest and capital expenditures). A similar number can be calculated from the recent analysis presented by Goldstein based on general plant tissue culture characteristics. Using Goldstein's 2000 kg product per year basis (which is implicitly 22 tons of cell mass based on assumed productivity), the fixed costs (calculated as capital charges) were 55.4% of the manufacturing costs. The estimate of Yoshioka and Fujita is likely to be more generally applicable since it uses a cycle time of roughly 14 days as compared to the 5-day reactor cycle time assumed by Goldstein. Clearly capital investment is an important target for cost reduction. This is not surprising since equipment and support facilities associated with aseptic bioprocessing are extremely expensive because vessels are constructed of stainless steel and pressure rated for autoclave sterilization. Accordingly, eliminating the need for expensive autoclave construction could substantially reduce production costs by reducing the initial capital investment.

SUMMARY OF THE INVENTION

In light of the foregoing, the present invention provides a method and apparatus for producing cells, tissues and/or microorganisms. The method includes providing a disposable liner forming a reservoir having an opening. A closure is attached to the liner to close the opening. The liner and attached closure are sterilized. A biomass dispersion is then introduced into the reservoir.

The present invention further provides a bioreactor for culturing cells, tissues and microorganisms. The bioreactor includes a support, and a liner mounted on the support and forming a reservoir for receiving a biomass dispersion. A closure sealingly engages the liner to close the liner opening. The closure sealingly engages the liner and is separable from the liner. The closure includes an inlet port in fluid communication with the reservoir.

DESCRIPTION OF THE DRAWINGS

The foregoing summary, as well as the following detailed description of the preferred embodiments, will be better understood when read in conjunction with the accompanying drawing, in which.

DETAILED DESCRIPTION OF THE PREFERRED EMBODIMENTS

Figure 1:
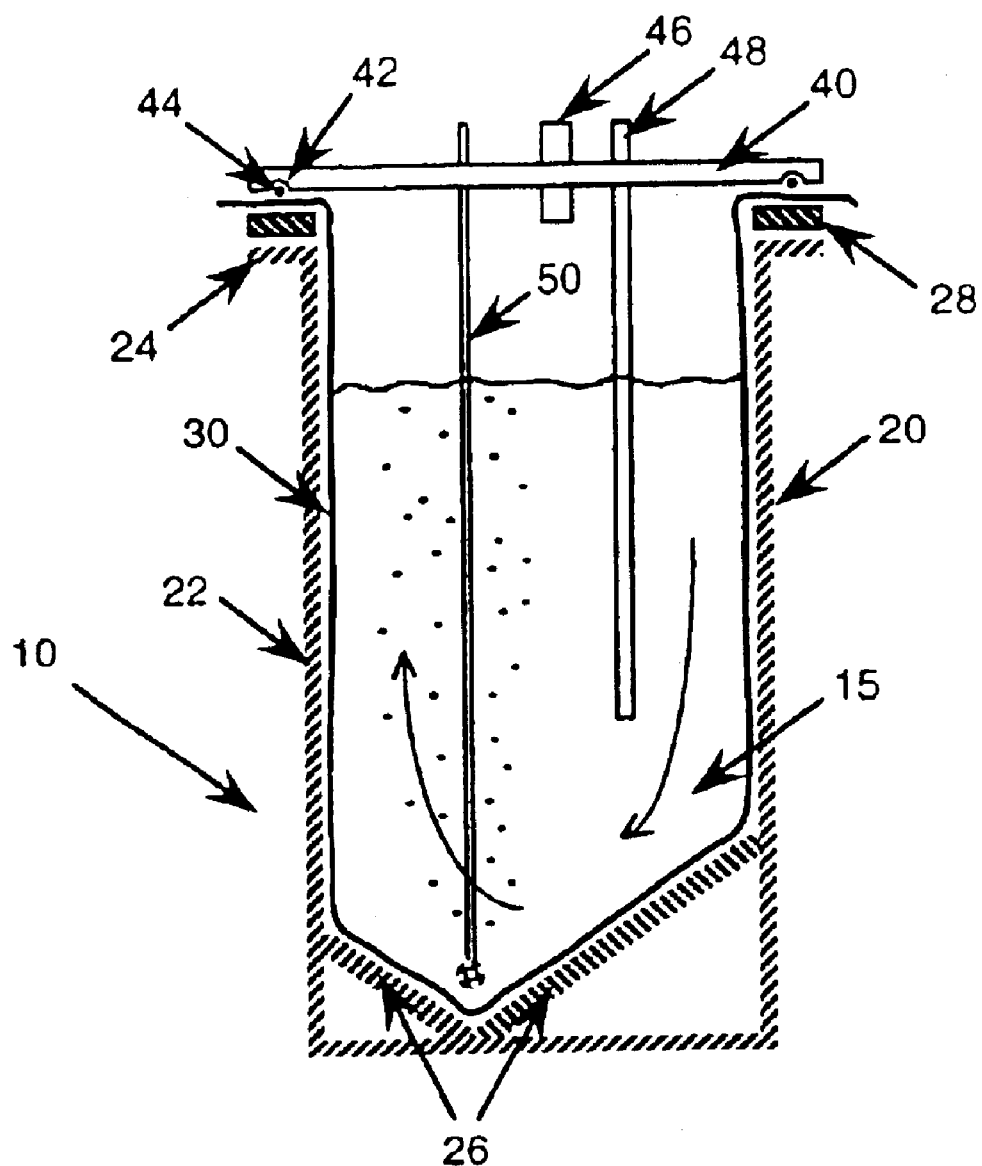
FIG. 1 is a side sectional view of an aseptic bioreactor in accordance with the present invention.

Referring now to the drawings in general, and to FIG. 1 specifically, an aseptic bioreactor 10 is illustrated. The bioreactor is lined with a disposable liner 30. The bioreactor is used for biological production of cells, tissues and/or microorganisms in a culture medium. After use, the cells and culture medium are removed from the bioreactor 10 and the liner 30 is disposed. The bioreactor can then be used again with a fresh liner.

The bioreactor 10 can be used to produce any of a number of microorganisms and/or cells, including, but not limited to bacteria, fungi, animal cells, nematodes and plant cells. In addition to the production of biomass, the bioreactor is operable to process biomass grown in alternative bioreactors or tissues produced by conventional non-aseptic methods, such as: animal husbandry, field growth plants or general biomass byproducts. Specifically, the bioreactor is operable in connection with biotransformation of biochemicals utilizing enzymatic capabilities of tissue-such as transgenic plant tissue grown in the field to express a heterologous enzymatic activity. The bioreactor is also operable in connection with expressing proteins from post-harvest activated promoters in which the biomass is grown in the field. In such circumstances, the tissue is not growing within the vessel, however, the viable tissue is carrying out the desired chemistry within a process vessel that can be of the type described herein.

In the following description, the bioreactor is described in connection with the production of plant cells. However, the design and/or operation of the bioreactor can be modified to accommodate production of other types of cells. For example, the production of plant cells progresses slowly so that respiratory heat removal is not problematic to maintain the proper temperature within the bioreactor. However, when producing microorganisms that exhibit rapid progression, such as bacteria, respiratory heat removal is generally necessary to maintain the proper temperature within the bioreactor. Therefore, to accommodate such an application, the bioreactor can be configured to include a heat exchange coil for heat removal. Accordingly, although the following description exemplifies use of the bioreactor in connection with producing plant cells, the bioreactor is not limited to such use.

The bioreactor 10 includes a hollow support housing 20 lined by the disposable liner 30. A head plate 40 is attached to the liner to form a sealed reservoir within the liner 30. The head plate 40 and liner 30 are then sterilized to form an aseptic environment within the reservoir. Culture medium is introduced into the container 20 through an inoculation tube 46 that is in fluid communication with the reservoir. The culture medium is then inoculated through the inoculation tube 46. An aerator 50 extends through the head plate 40 to aerate the biomass dispersion during the production cycle. During the production cycle, the reservoir is sealed to prevent contamination from the outside environment. After the production cycle is complete, the biomass dispersion is removed from the reservoir. After the biomass dispersion is removed, the liner 30 is disposed. Since the liner 30 prevents the biomass dispersion from coming into contact with the support housing 20, the support housing need not be sterilized before reusing the bioreactor for another production cycle. Instead, the reusable head plate 40 is attached to a new liner, and the two are sterilized. In this way, the sterilization of the bioreactor is simplified, and validation of the "clean in place" procedures is significantly simplified.

STRUCTURE OF THE APPARATUS

The structure of the bioreactor 10 will now be described in greater detail. The support housing 20 is an elongated hollow generally cylindrical container. The upper end of the support housing is generally open and the lower end or bottom of the support housing is closed. In the present instance, the support housing 20 includes a circumferential flange 24 projecting outwardly from the side walls 22 of the housing. Baffles 26 are disposed in the interior of the support housing 20 adjacent the bottom on the support housing. As shown in FIG. 1, the baffles 26 form an asymmetric or offset V-shape. As discussed in more detail below, the V-shape improves circulation of the bioreactor.

The support housing 20 can be configured in almost any shape. If an "air-lift" circulation system is utilized as described below, preferably, the aspect ratio of the container is such that the height is 2 to 5 times the width of the container. However, the aspect ratio may be higher or lower. For instance, in certain situations it may be desirable to use a support housing that is shallow and wide. For such a shallow support housing, the fluid pressure of the aeration fluid can be reduced because the pressure at the bottom of a shallow reservoir is less than that of a deeper reservoir, and the aeration fluid must overcome this fluid pressure to aerate the reservoir.

The support housing 20 may be formed of glass thereby exposing the biomass dispersion 15 to light, and allowing visual inspection of the biomass dispersion. However, the support housing can also be formed of any number of materials including metal or plastic. In addition, the support housing can be opaque or semi-opaque.

As can be seen from the foregoing, the configuration of the support housing 20 can be varied considerably. Generally, a structure that mechanically supports the weight of the cell suspension 15 can be utilized. Specifically, a structure that supports the vertical force of the weight of the cell suspension 15 and the lateral or horizontal force of the fluid pressure of the biomass dispersion can be utilized. For instance, the support housing 20 could be in the form of an open framework or mesh rather that the solid walls of the housing shown in FIG. 1.

The liner 30 is preferably formed of plastic. The plastic may be transparent or translucent to allow light into the reservoir and to permit visual inspection of the bioproduction/bioprocessing if desired. The type and thickness of plastic will depend upon several variables, including the size of the support housing 20 and the type of sterilization process that will be utilized to sterilized the liner 30 and the head plate 40. For instance, a 2 mil thickness autoclavable polypropylene bag can be utilized if autoclaving is used. For other sterilization processes, such as gas-phase or plasma-phase sterilization, the liner 30 may be formed of a 6 mil thickness polyethylene bag.

A shown in FIG. 1, the area in the support housing 20 above the baffles 26 and between the side walls 22 forms an internal chamber. The liner 30 lines this internal chamber to prevent the cell suspension 15 from coming into contact with the interior of the support housing 20. The upper edge of the liner 30 overlays the flange 24 at the top of the support housing 20. The upper edge of the liner 30 may be sandwiched directly between the head plate 40 and the flange 24. However, in the present instance, the upper edge of the liner 30 is disposed between the head plate and a support ring 28 that rests on the flange 24. The support ring 28 is a flat ring that is approximately as wide as the flange 26 of the support housing. By sandwiching the upper edge of the liner 30 between the head plate 40 and the support ring 28, the head plate and liner can be removed from the support housing without detaching the liner from the head plate.

The head plate 40 is a substantially round plate having a diameter that is greater than the open end of the support housing 20. The head plate can be made from a variety of materials including metal and plastic. For instance, the head plate 40 may be formed of polycarbonate. The lower surface of the head plate 40 confronts the upper surface of the support ring 28. Preferably, a sealing groove 42 extends around the periphery of the lower surface of the head plate, spaced inwardly from the outer edge of the plate. A seal 44 in the form of an O-ring is disposed in the sealing groove 42. The head plate 40 can be attached to the sealing ring 28 in any of a number of ways. Preferably the head plate is releasably attached to the sealing ring 28 so that the liner 30 can be detached from the head plate, allowing the head plate to be reused. In the present instance, the head plate 40 is clamped to the sealing ring 28 with the upper edge of the liner 30 disposed between the head plate and the sealing ring. In this way, a fluid-tight seal is provided between the head plate and the opening in the liner.

The bioreactor 10 includes an inoculation tube 46 and a sampling tube 48 that project into the sealed reservoir formed by the liner 30 and the head plate 40. The inoculation tube 46 and the sampling tube 48 are in fluid communication with the sealed reservoir and provide access to the interior of the bioreactor from exterior of the bioreactor. A seal is formed between the exterior of the inoculum and sampling tubes 46, 48 and the head plate to provide a fluid-tight seal. The inoculation tube 46 is of sufficient diameter for introducing the culture medium into the sealed reservoir through the inoculation tube, along with the inoculum. Depending on the application, the inoculation tube can be configured in any one of a number of designs that facilitate introducing inoculum and resealing the inoculation tube to prevent contamination. The sampling tube is of sufficient diameter for withdrawing media samples.

The bioreactor 10 further includes an aerator 50. In the present instance, the aerator is a sparger. A filter is provided for filtering the gas used by the aerator to prevent contaminants from entering the reservoir. As shown in FIG. 1, the aerator projects through the head plate 40 and into the bottom of the reservoir. For submerged cultures, the aerator 50 is preferably aligned with the vertex of the V-shaped bottom of the reservoir formed by the baffles 26 in the bottom of the support housing 20. In the present instance, the aerator 50 includes two spargers attached in a T-configuration that is parallel to the crease in the V-shaped baffle 26.

In the present instance, the aerator 50 also operates to circulate the biomass dispersion within the bioreactor 10. This is referred to as an "air-lift reactor." The gas bubbling through the biomass dispersion 15 from the aerator 50 causes variations in the density of the culture medium. This operates to circulate the culture medium in the reservoir. For this reason, it is desirable to have the bottom end of the aerator 50 adjacent the lowest point of the reservoir.

The bottom of the reservoir may be flat. However, to improve circulation it is desirable to eliminate the lower corners that form dead spaces. For this reason, the baffle 26 is V-shaped. Offsetting the vertex of the V-shaped baffle 26 as shown in FIG. 1 further improves the circulation in the reservoir. In addition, in a large bioreactor it may be desirable to include a plurality of aerators to improve aeration and circulation.

As described above, in the present instance the aerator 50 operates as an aerator and a circulator. In certain instances it may be desirable to further include a separate circulator. For instance, an impeller can be included to improve the circulation in the reservoir. Such an impeller can be journalled in a bearing mounted in the head plate so that it extends downwardly into the bottom of the reservoir.

As another example, a magnetic impeller may be provided to improve the circulation in the reservoir. A magnetic impeller would not require the mechanical connection between the impeller blade and the drive mechanism. The magnetic impeller utilizes magnetic force to drive the impeller blade. Since there is no mechanical connection between the magnetic impeller blade and the impeller drive, there is no need to provide an additional seal as is required around the drive shaft of a standard impeller. In addition, since magnetic impeller blades can be relatively inexpensive, the magnetic impeller blade can be disposed along with the liner 30 after a production cycle is completed. This further simplifies cleaning the apparatus and preparing for a subsequent production cycle.

Figure 3:
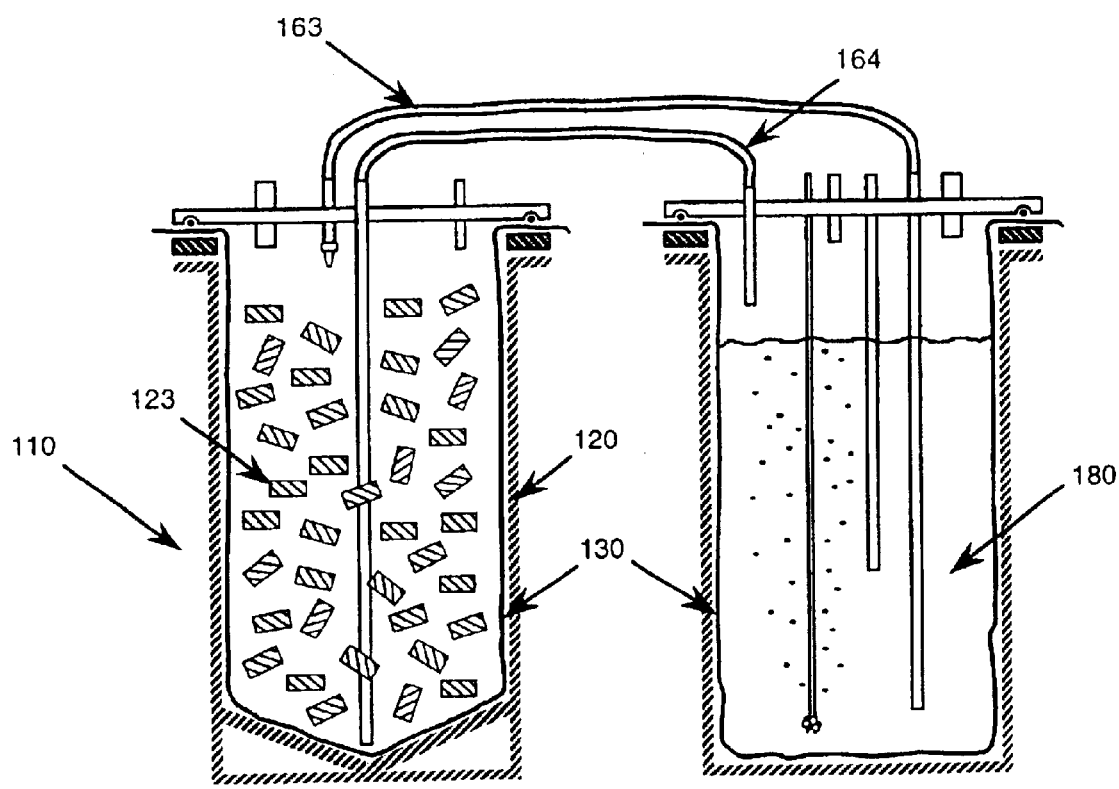
FIG. 3 is a side sectional view of second embodiment of an aseptic bioreactor in accordance with the present invention.

The embodiment illustrated in FIG. 1 shows a gas-dispersed liquid culture. However, the process can also be implemented as a liquid-dispersed bioreactor in which medium is dispersed over the top of the biomass. For example, referring to FIG. 3, an alternative bioreactor embodiment 110 is illustrated. In the alternative embodiment, the biomass is in a primary reservoir and fluid is circulated into the primary reservoir from a secondary reservoir 180 that is separate from the primary reservoir.

Specifically, the bioreactor 110 includes a reservoir lined by a disposable liner 130 that lines a support 120. A head plate 140 seals the liner as in the first embodiment and forms a primary reservoir for growing or processing a biomass. Preferably, a bed of material 123, such as industrial process packing is introduced into the primary reservoir and culture medium is circulated through the reservoir.

A secondary reservoir 180 is also provided. Preferably, the secondary reservoir is also formed by a disposable liner that lines a support and is sealed by a head plate. The secondary reservoir contains a quantity of fluid, which may be culture medium or biomass dispersion as is discussed further below.

A feed line 163 and return line 164 are provided for recirculating fluid between the primary and secondary reservoirs. The feed line and return line are in fluid communication with the primary and secondary reservoirs. The return line 164 extends into the bottom of the primary reservoir to recycle fluid after it flows through the primary reservoir.

In this way, a "trickle bed" can be utilized to grow or process biomass. Specifically, biomass is introduced into the primary reservoir. Culture medium is circulated through the primary reservoir from the secondary reservoir. If a bed of material 123 is provided, the culture medium flows into the primary reservoir over the bed of material 123. The culture medium trickles through the bed of material and is then recycled through the return line 164. As the fluid flows through the primary reservoir over the bed of material 123, the fluid promotes the growth or processing of the biomass in the bed of material.

Depending on the biomass, the circulated fluid can be either culture medium alone or biomass dispersion. Specifically, if the biomass dispersion is a suspension, then the suspension is circulated from the secondary reservoir, into the primary reservoir, over the bed of material, and then recycled through the return line 164. In other applications, the biomass dispersion may not be a suspension. In such applications, substantially all of the biomass remains in the primary reservoir and culture medium is circulated over the biomass.

The re-circulating system has been described in connection with a bed of industrial process packing through which the culture medium or biomass dispersion circulates to promote growth or processing of biomass in the bed. However, the bedding material need not be industrial process packing. The bedding material can be other granular material or matrix material.

In addition, the recirculating system is operable in certain applications without a bed of material. In such applications, the biomass is introduced into the primary reservoir, and culture medium is circulated over biomass.

METHOD OF OPERATION

The bioreactor 10 operates as follows. The head plate 40 and liner 30 are attached and sterilized to form an aseptic container. The head plate and liner can be sterilized in any of a number of ways. For instance, autoclaving can be used if the liner 30 and head plate are formed of materials that withstand the temperature and pressure of the autoclaving process. Alternatively, the head plate and liner can be sterilized by gas-phase sterilization using ethylene oxide gas in accordance with hospital guidelines for ethylene oxide sterilization of medical devices. In addition, other sterilization processes such as a vapor phase oxidant, plasma or radiation sterilization.

Furthermore, although the operation of the device contemplates the ability to be sterilized in accordance with the stringent guidelines of the pharmaceutical industry, the term sterilization as used herein is not limited to pharmaceutical or medical sterility. The term sterilization is meant to include cleaning to less stringent standards such as the standards for sterility for the food industry. In addition, as used in this description, the term sterilization is also meant to include marginal sterility, meaning reduction or suppression of non-productive contaminating organisms to sufficiently low numbers so that their presence does not prevent or significantly impede the desired biomass growth or processing. Accordingly, as can be seen from the foregoing, operation of the bioreactor is not limited to a particular sterilization process.

If sterilization is to be used, the head plate 40 and attached liner 30 can be inserted into the autoclave without the support housing because the support housing need not be sterilized since it does not come into contact with the biomass dispersion. Accordingly, a liner and head plate can be autoclaved in a collapsed state, so that a smaller autoclave vessel can be utilized to service a plurality of large-scale production bioreactor tanks. If gas-phase sterilization is to be used, the head plate is attached to the liner, a gas mixture of ethylene oxide and carbon dioxide is introduced into the sealed reservoir formed by the head plate and liner. Preferably, prior to introducing a gas into the reservoir, steam is introduced into the reservoir to provide a damp environment and assure hydration of contaminant spores. After gas-phase sterilization, the toxic ethylene oxide is removed by aeration using a slow flow of air. Surface sterilant gases such as hydrogen peroxide may require little or no aeration.

During gas-phase sterilization, the ethylene oxide gas can permeate the liner 30 and accumulate between the liner and the inner wall of the support housing 20. This accumulated ethylene oxide may remain in the bioreactor after standard aeration procedures. This residual ethylene oxide can permeate through the liner 30 into the reservoir during the production cycle to adversely affect cell production. Accordingly, it is desirable to minimize the gap between the liner and the inner wall of the support housing. In addition, it is desirable to aerate the inside and outside of the liner and head plate assembly to reduce the amount of residual ethylene oxide. This can be accomplished by removing the sealed head plate and attached liner assembly from the support housing and aerating the support housing in addition to aerating the reservoir. It should be noted that potential toxicity of residual ethylene oxide release will become less significant for larger scale reactors since the film surface area to tank volume rapidly declines with scale-up. In addition, the use of non-permeating surface sterilant gas could greatly reduce aeration considerations for gas or plasma phase sterilization.

After the liner and head plate assembly are sterilized, the liner is inserted into the support housing. Alternatively, depending on the type of sterilization used, the liner and head plate assembly can be inserted into the support and then sterilized. Culture medium is then introduced into the sealed medium through the inoculation tube 46. If desired, a growth regulator is also introduced into the reservoir through the inoculation tube. This combination is then inoculated with a cell culture. For clarity, the resultant mixture of cell culture, growth regulator, if any, and culture medium are referred herein to as a biomass dispersion. The biomass dispersion is aerated by the aerator 50 during the production cycle.

The biomass growth is monitored during the production cycle so that the composition of the aeration fluid and/or the flow rate of the aeration fluid can be adjusted to optimize cell growth. Depending on the cell or microorganism being produced, the characteristics monitored during the production cycle may vary. For instance, utilizing dissolved oxygen as a control parameter may be desirable for rapid-production cultures such as bacteria. Conversely, using dissolved oxygen as a control parameter for slow-production cultures, such as plant tissue cultures, can be problematic. Similarly, off-gas analysis can be used to monitor respiration. However, off-gas analysis is generally more amenable to monitoring rapid-production cultures then slow-production cultures. Nonetheless, other measurements indicative of biomass growth can be utilized to effectively monitor biomass growth of slow-production cultures. For instance, in certain culture media, the refractive index of the culture medium is an indicator of sugar levels, and the electrical conductivity of the culture medium is an indicator of inorganic nutrients. These characteristics can be measured and used to correlate biomass accumulation based on nutrient consumption. The examples detailed below describe plant tissue production, utilizing refractive index and electrical conductivity and medium osmolality as control parameters. These details of such production control are set forth in greater detail in Ramakrishnan, D.; Luyk, D.; Curtis, W.R., "Monitoring biomass in root culture systems", Biotechnology and Bioengineering, 62 (6): 711–721, 1999, which is hereby incorporated herein by reference as is fully set forth herein.

None of these measurements mentioned above require introduction of a measuring instrument into the reservoir. However, if the bioreactor is utilized to produce other types of cells and/or organisms, the bioreactor may include one or more measuring devices that extend into the reservoir, preferably through the head plate in a fluid-tight relation, to prevent introduction of contaminant cells and/or microorganisms. For instance, a pH meter may be attached to the head plate, extending downwardly into the reservoir to monitor the pH of the culture medium.

In response to the measured characteristic, the operating environment may be modified to optimize biomass production or processing. For instance the gas composition of the aeration gas can be modified. Alternatively, the flow rate of the aeration gas can be varied. In addition, the biomass dispersion may be supplemented with sugar and/or inorganics to encourage continued growth.

EXAMPLE 1

Two 9 L (6.5 L working volume, w.v.) bioreactors were provided: one steam autoclave sterilizable and the other ethylene oxide (EtOX) sterilizable. For the autoclavable configuration, the plastic liner was a 2 mil polypropylene autoclavable bag (25 cm width by 46 cm height). The top edge of the bag was clamped to a 12.7 mm thickness polycarbonate head plate which contained a 17 mm internal diameter (ID) stainless steel inoculation tube, a 1.4 mm ID tube for withdrawing medium samples, a 4.5 mm ID gas outlet tube, and an additional 4.5 mm ID tube which extended to the bottom of the bag with a 0.2 micron sintered metal mobile phase sparger attached for sparging of gas. A bead of hot melt glue stick was applied between the bag and head plate, which melted upon autoclaving to provide an air-tight aseptic seal. The reactor was steam sterilized at 121° C. for 30 minutes in a collapsed state, and expanded after autoclaving inside a 15.2 cm diameter non-sterile glass vessel.

EXAMPLE 2

The second bioreactor is designed to eliminate the need for autoclave sterilization. The second bioreactor utilizes sterilization through exposure to ethylene oxide (EtOX)-carbon dioxide gas mixture. The ability to sterilize the reactor without high temperature eliminated the need for autoclavable materials. For this reason, the plastic liner was constructed from 6 mil thickness polyethylene, and Norprene tubing was used in all connections to minimize degradation and diffusion of EtOX during the sterilization cycle. The liner was constructed to fit inside the same 15.2 cm ID (internal diameter) glass column, with the seams sealed with a hot glue gun and a hand iron wrapped in paper towel. The head plate was constructed from 20-gauge (0.95 mm) 304 stainless steel sheet metal where the ports analogous to those described for the polycarbonate head plate were silver-soldered in place. The head plate and liner were held in place by bolting through the collar of the Corning conical glass connections. A bead of silicone glue was applied between the headplate and plastic to facilitate the seal. Gas-phase sterilization was accomplished using a commercially available mixture of ethylene oxide: 10% EtOX in carbon dioxide to avoid the danger of flammability. Prior to gas introduction, steam under ambient conditions was briefly introduced from the release valve of a commercial pressure cooker. This pre-sterilization steam treatment provided a damp environment and assured hydration of contaminant spores. Exposure to ethylene oxide was accomplished in a fume hood where roughly four reactor volumes of the EtOX gas mixture were introduced three times over a period of two days. Gas was introduced through the air sterilization filter, and the gas outlet was rotated using pinch clamps through the medium sample, gas outlet, and inoculation ports. After gas-phase sterilization, the toxic EtOX was removed by a slow flow of 200 mL/min of sterile air for a period of roughly two days based on hospital guidelines for ethylene oxide sterilization of medical devices.

EXAMPLE 3

A 40 L bioreactor with a working volume (w.v.) of 28.5 L was constructed from 6 mil plastic to fit inside a 59.7 cm height by 28.3 cm diameter glass tank. The head plate sealed against a compression ring so that the liner and head plate could be independently removed from the tank to facilitate aeration from both sides of the liner and eliminate pockets of ethylene oxide between the liner and the support tank. Circulation was facilitated by off-center placement of the sparger, and contouring of the tank bottom with a baffle. The baffle was 'V'-shaped with the crease off-center to align with the sparger. The sparger consisted of two 0.2 micron sintered metal mobile phase spargers attached in a T-configuration so that they could be placed parallel to the crease in the V-shaped baffle. The reactor was fitted with a 28.6 mm ID inoculation port and 9.5 mm ID sample port similar to the other reactor configurations. The 34 cm ID head plate and compression ring were constructed of 12.7 mm thickness polycarbonate with an o-ring groove machined in the upper plate 25.4 mm from the edge to provide for a seal against the plastic liner.

EXAMPLE 4

A 150 L (100 L w.v.) bioreactor was constructed from 6 mil polyethylene film to fit inside a 85.7 cm height by 45.1 cm diameter stainless steel process tank. The baffling geometry, head plate compression ring, and sparging arrangement were analogous to Example 3. The polycarbonate head plate included a 19.1 mm ID inoculum port, and two 12.7 mm ID compression fittings for the sparge tube inlet and sample port. A separate 6.4 mm ID compression fitting was used for gas outlet. A thin silicone film on the 5.7 cm width aluminum compression flange 28 was utilized to accomplish the seal between the head plate and plastic liner.

The root culture used in EXAMPLE 4 was culture of *Hyoscyamus muticus*, line HM90T, established by *Agrobacterium rhizogenous* transformation in 1990 and grown on "Gamborg B5" medium. The cell suspension line used for the four EXAMPLES was established from the same root culture by de-differentiating the root culture through the addition of 0.2 mg $L^{-1}$ of the growth regulator 2,4 dichlorophenoxyacetic acid (2,4 D). The root line and cell lines have been maintained for more than 3 years through serial bi-weekly subculturing on their respective medium. Autoclaved B5 medium was introduced aseptically for Examples 1 through 3, and Example 4 utilized filter sterilization through a cartridge filter sterilization unit. The initial medium volumes were 6.5 L (Example 1), 6.7 L (Example 2), 28.5 L (Example 3) 100 L (Example 4, for both cell and root culture run).

The operational strategy for the bioreactors relied upon the refractive index and conductivity (as well as visual observation through the glass reactor) for making operational changes. The initial gas flow rate to the prototype reactors was minimized (0.05 volumes of gas per volume of medium per minute, VVM) corresponding to 0.33 liters per minute. Air was used for the first day to avoid potential problems of oxidative stress and the low flow rates reduced foam fractionation and loss of cells on the reactor vessel walls at the surface of the medium. When the conductivity started to decline indicating culture growth—the gas composition was changed to 30–40% oxygen in air by oxygen supplementation. This oxygen enrichment permitted low gas flow rates and minimized wall growth. The gas flow rate was incrementally increased to 0.25 VVM for the 9 L autoclaved bag and 0.20 VVM for the 9 L EtOX sterilized bag as the culture nutrients declined. The gassing program for the 40 L reactor was initiated at 0.05 VVM, and incrementally increased to 0.25 VVM as the culture nutrients declined. CO and O supplementation for the 40 L reactor were initiated at day 2 and 10, respectively. The glass support tank permitted visual observation, which confirmed that the gas flow should be increased more rapidly in the air-lift reactors than the gas-flow used in a typical stirred tank to avoid cell sedimentation.

The gassing strategy in the 150 L bioreactor paralleled that of the smaller reactors. This pilot-scale run was undertaken to verify the utility of nutrient feed based on the measurements of media conductivity, refractive index and osmotic pressure. When refractive index and conductivity indicated 90% nutrient consumption (day 9 after inoculation), a sucrose feed corresponding to an additional 20 g sucrose per liter was added to the bioreactor. The root culture was operated in simple batch mode without media supplementation.

RESULTS

Figure 2A:
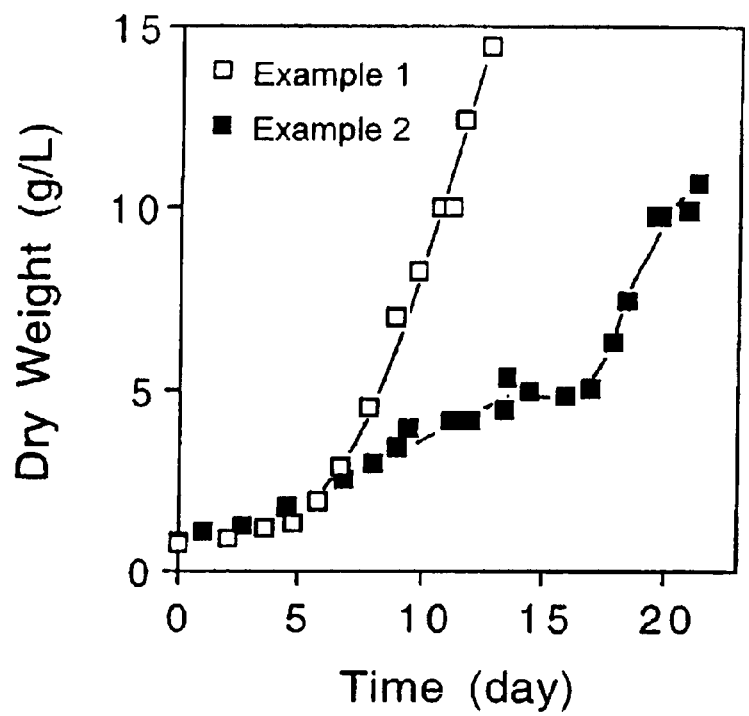
FIG. 2a is a graph of the growth of the cell cultures for Examples 1 and 2.

Biomass accumulation for the two smaller vessels is plotted in FIG. 2a. Growth ceased in the EtOX sterilized reactor in Example 2 due to sugar depletion as indicated by a zero refractive index for the final cell concentration data points. The autoclaved reactor in Example 1 also reached a zero RI; however, a supplementation of sugar was added at day 11, which permitted continued growth. This indicated that substantially higher cell concentrations are possible. The autoclaved bag reactor was terminated when a low-level contaminant was observed at day 13 as the appearance of slow growing colonies on LB media plates.

Growth in the ethylene oxide sterilized reactor in Example 2 was clearly attenuated—presumed to be due to toxicity of residual ethylene oxide. Based on recommendations for hospital use of EtOX, it was anticipated that the two days aeration period should have been adequate for removal of residual EtOX. However, it was later realized that the sand below the plastic bag could have acted as a reservoir that would diffuse small amounts of residual EtOX for a long period of time. After 15 days of slow growth, the rapid consumption of nutrients indicated a rapid growth period, which was visually evident through the glass reactor as well, suggesting a recovery from the ethylene oxide toxicity.

Figure 2B:
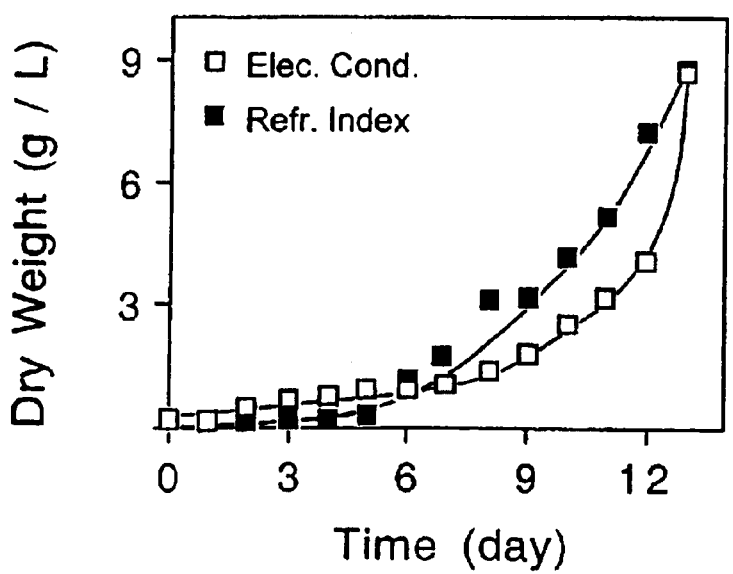
FIG. 2b is a graph of the growth of the cell culture for Example 3.

As discussed previously, residual sterilant gas removal predicated that the potential for residual toxicity can be minimized for a well fit reactor liner. For the Third Example, the contouring of the support housing was accomplished by baffles which resulted in large reservoir volumes between the liner and the tank wall. The design of the 40 L bioreactor permitted removal of the liner and head-plate from the tank to provide aeration on both sides. AS shown in FIG. 2b, this successfully eliminated the long lag observed in the smaller prototype reactor in Examples 1 and 2, and the specific growth rate of 0.26 $day^{-1}$ is approximately the same as the results for stirred tank bioreactors. The bioreactor of the Third Example produced 2.9 Kg FW (199 g DW) of cells in 13 days.

The 150 L bioreactor with sugar supplementation produced over 53.8 Kg fresh weight (1.5 Kg DW) of plant cell suspension biomass during the 33 day culture period. This represents one of the highest biomass productivities achieved in plant cell culture at the pilot scale. This run demonstrated the ease of scaleability of the bioreactor and utility of the monitoring technique. By the end of the run, more than half of the water within the bioreactor was inside the biomass so that more simplified methods of attempting to monitor bioreactor performance based on media concentrations were not accurate. The same reactor inoculated with homogenized root tissue produced 24.1 g FW Kg FW (881 g DW) or root tissue for a 31 day culture period. The growth of root cultures demonstrates the versatility of the bioreactor in growing an organized tissue.

The method and apparatus of the present invention provide a simple, low cost bioreactor for bench and pilot scale discovery and developmental studies. A plastic lined reactor has very attractive characteristics besides the reduction in costs. Such a design could potentially eliminate much of the costs associated with validation of clean in place (CIP) procedures since the plastic liner portion of the reactor is disposable. Validation of sterilization only requires verifying sterilization of the reusable head plate, and a clean plastic liner. Accordingly, the method and apparatus of the present invention should be capable of meeting the very stringent cGMP (good manufacturing practices) guidelines currently imposed on the pharmaceutical industry.

Costs for gas sterilization could be improved by sterilization in a collapsed state to minimize gas use. Similarly, the bag and head plate assembly could be autoclaved in a collapsed state—thereby utilizing one smaller autoclave-type vessel to service many larger-scale production tanks.

It will be recognized by those skilled in the art that changes or modifications may be made to the above-described embodiments without departing from the broad inventive concept of the present invention. For instance, the bioreactor may be utilized for anaerobic fermentation. For such production, the bioreactor need not include means for aerating or circulating the cell suspension in the reservoir. Accordingly, it should be understood that the present invention is not limited to the particular embodiments described herein but is intended to include all changes and modifications that are within the scope and spirit of the invention as set forth in the claims.

What is claimed is:

1. A method for culturing one or more cell or microorganism, comprising the steps of:
   providing a flexible sterile plastic liner forming a reservoir;
   introducing a culture media into the reservoir;
   inoculating the culture media with one or more cell or microorganism to provide a cell suspension for culturing the cell or microorganism;
   aerating the cell suspension with a aerating fluid at a flow rate wherein the aerating fluid comprises a gas;
   detecting a growth characteristic of the cell or microorganism in the cell suspension; and
   varying the flow rate and/or the composition of the aerating fluid in response to the detected characteristic.

2. The method of claim 1 comprising the step of releasing aerating fluid from the reservoir.

3. The method of claim 1 comprising the step of circulating the cell suspension.

4. The method of claim 1 wherein the reservoir comprises an opening and the method comprises the step of providing a closure having a port in fluid communication with the reservoir, wherein the closure forms a fluid-tight seal with the reservoir to seal the opening.

5. The method of claim 4 wherein the step of inoculating comprises inoculating the culture media through the port in the closure.

6. The method of claim 4 wherein the step of aerating comprises aerating the cell suspension through the port in the closure.

7. The method of claim 1 wherein the step of aerating comprises bubbling the aerating fluid through the cell suspension.

8. The method of claim 4 comprising the step of circulating the cell suspension through the port in the closure.

9. The method of claim 1 comprising the step of sealing the reservoir to prevent a contaminant cell or microorganism from entering the reservoir.

10. A method for culturing one or more cell or microorganism, comprising the steps of:
    providing a disposable first flexible sterilized plastic liner forming a reservoir having an opening;
    attaching the first liner to a closure to close the opening;
    introducing into the reservoir a cell suspension comprising culture medium and one or more cells or microorganisms;
    culturing the cell or microorganism in the reservoir;
    detaching the first liner from the closure after culturing the cell or microorganism; and
    attaching a second flexible sterilized plastic liner to the closure after detaching the first liner.

11. The method of claim 10 comprising the step of aerating the cell suspension with a fluid at a flow rate.

12. The method of claim 10 comprising the step of circulating the culture medium within the reservoir.

13. The method of claim 11 comprising the step of detecting a growth characteristic of the cell or microorganism in the cell suspension and varying the aerating fluid composition in response to the detected characteristic.

14. The method of claim 13 wherein the reservoir is translucent, and the step of detecting a growth characteristic comprises optically detecting a characteristic of the cell suspension while the cell suspension is in the reservoir.

15. The method of claim 11 comprising the step of detecting a growth characteristic of the cell suspension and varying the aerating fluid flow rate in response to the detected characteristic.

16. The method of claim 15 wherein the reservoir is translucent, and the step of detecting a growth characteristic comprised optically detecting a characteristic of the cell suspension while the cell suspension is in the reservoir.

17. A method for culturing cells and/or a microorganism, comprising the steps of:
    providing a first flexible sterile plastic lining forming a reservoir having a first opening:
    introducing a culture media into the first reservoir;
    introducing cells or a microorganism into the first reservoir;
    closing the first opening so that the first opening is substantially closed while maintaining a port for fluid transfer into the first reservoir;
    providing a second reservoir having a culture media;
    circulating the culture media between the first reservoir and the second reservoir through the port in the first opening.

18. The method of claim 17 comprising the step of circulating the culture media within the second reservoir.

19. The method of claim 17 comprising the step of circulating the culture media within the second reservoir with an aerating fluid.

20. The method of claim 17 comprising the step of aerating the cells or microorganism with a fluid.

21. The method of claim 20 wherein the cells or microorganism are aerated by aerating the culture media in the second reservoir.

22. The method of claim 20 wherein the culture media and the cells or microorganisms are combined to form a cell culture, wherein the method comprises the step of detecting a growth characteristic of the cell or microorganism in the cell culture and varying the flow rate and/or composition of the aerating fluid.

23. The method of claim 22 wherein the method comprises varying the flow rate of the aerating fluid.

24. The method of claim 22 wherein the method comprises varying a composition of the aerating fluid.

25. The method of claim 22 wherein one of the first and second reservoirs are translucent and the step of detecting a characteristic comprises optically detecting a characteristic of the cell culture while the cell culture is in the one of the first and second reservoirs.

26. The method of claim 17 wherein the second reservoir is formed of a flexible plastic liner having a second opening.

27. The method of claim 17 wherein the step of closing the first opening comprises releasably sealing the first opening.

* * * * *

UNITED STATES PATENT AND TRADEMARK OFFICE
CERTIFICATE OF CORRECTION

PATENT NO. : 6,709,862 B2
DATED : April 7, 2004
INVENTOR(S) : Wayne R. Curtis

It is certified that error appears in the above-identified patent and that said Letters Patent is hereby corrected as shown below:

Column 11,
Lines 35 and 36, "CO and O" should read -- $CO_2$ and $O_2$ --;

Column 14,
Line 16, "plastic lining forming" should read -- plastic liner forming --;
Line 57, "a flexible plastic" should read -- a flexible sterile plastic --;

Signed and Sealed this

Twenty-fifth Day of January, 2005

JON W. DUDAS
*Director of the United States Patent and Trademark Office*

UNITED STATES PATENT AND TRADEMARK OFFICE
CERTIFICATE OF CORRECTION

PATENT NO. : 6,709,862 B2  Page 1 of 1
DATED : March 23, 2004
INVENTOR(S) : Wayne Curtis It is certified that error appears in the above-identified patent and that said Letters Patent is hereby corrected as shown below:

Column 1,
Line 13, insert the following:
-- This invention was made with support from the Government under Grant No. BES-9522033. The Government has certain rights in the invention. --.

Signed and Sealed this

Twenty-first Day of March, 2006

JON W. DUDAS
*Director of the United States Patent and Trademark Office*